(12) United States Patent
Tagliabue

(10) Patent No.: US 9,403,058 B2
(45) Date of Patent: Aug. 2, 2016

(54) REAL-TIME COMPARISON OF ATHLETIC INFORMATION

(71) Applicant: NIKE, Inc., Beaverton, OR (US)

(72) Inventor: Roberto Tagliabue, Lake Oswego, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 14/257,077

(22) Filed: Apr. 21, 2014

(65) Prior Publication Data

US 2014/0228989 A1 Aug. 14, 2014

Related U.S. Application Data

(63) Continuation of application No. 12/031,941, filed on Feb. 15, 2008, now Pat. No. 8,727,947.

(60) Provisional application No. 60/890,223, filed on Feb. 16, 2007.

(51) Int. Cl.
A63B 71/00 (2006.01)
A63B 15/02 (2006.01)
(Continued)

(52) U.S. Cl.
CPC ......... *A63B 24/0003* (2013.01); *A63B 24/0062* (2013.01); *A63B 69/0028* (2013.01);
(Continued)

(58) Field of Classification Search
CPC ............... A63B 24/00; A63B 24/0062; A63B 2225/50; A63B 2225/20; A63B 2230/062; A63B 2024/0068; A63B 2022/002; A63B 2024/0009; A63B 2220/30; A63B 24/0006; A63B 24/0075; A63B 24/0084; A63B 2024/0078; A63B 2071/0625; A63B 71/0686; A63B 2230/065; A63B 2024/0065; A63B 2230/067; A63B 2071/0663; A63B 71/0622; A63B 2230/00; A63B 2071/063; A63B 2220/62; A63B 69/3635; A63B 24/0003; A63B 69/0028; A63B 22/0605; A63B 22/0664; A63B 69/06; A63B 22/02; A63B 2230/06; A63B 2220/40; A63B 2024/0012; A63B 2071/0627; A61B 2503/10; A61B 5/0002; A61B 5/1118; A61B 5/1126; A61B 5/222; G06F 1/1684; G06F 1/163; G06F 1/1632; G06F 3/002; G01S 19/19; H04M 1/72527
USPC .................................................. 482/1, 3, 7, 8
See application file for complete search history.

(56) References Cited

U.S. PATENT DOCUMENTS 3,797,010 A 3/1974 Adler et al.
4,220,996 A 9/1980 Searcy
(Continued)

FOREIGN PATENT DOCUMENTS

EP 1847304 A1 10/2007
JP H10-63265 A 3/1998
(Continued)

OTHER PUBLICATIONS

Notification of Reexamination for Chinese Patent Application No. 200810005936.8 mailed Nov. 19, 2014.
(Continued)

*Primary Examiner* — Oren Ginsberg
*Assistant Examiner* — Shila Jalalzadeh Abyan
(74) *Attorney, Agent, or Firm* — Banner & Witcoff, Ltd.

(57) ABSTRACT

An apparatus compares athletic information relating to a user performing an athletic activity. The apparatus has a module (503, 505, 509) that generates a first set of athletic data corresponding to athletic information corresponding to the athletic activity performed by the user. The module has a memory (511) storing a second set of athletic data. The module compares the first set of athletic data to the second set of athletic data and communicates content to the user based on the comparison of the first set of athletic data to the second set of athletic data. The apparatus also has a module (803, 805) that determines the expected time of athletic activity and selects a set of feedback data having a duration proximate the expected time of athletic activity, wherein the module communicates the selected set of feedback data to the user.

6 Claims, 10 Drawing Sheets

(51) Int. Cl.

| | | |
|---|---|---|
| *A63B 24/00* | (2006.01) | |
| *A63B 69/00* | (2006.01) | |
| *G01S 19/19* | (2010.01) | |
| *G06F 1/16* | (2006.01) | |
| *G06F 3/00* | (2006.01) | |
| *A63B 22/02* | (2006.01) | |
| *A63B 22/06* | (2006.01) | |
| *A63B 69/06* | (2006.01) | |
| *A63B 71/06* | (2006.01) | |
| *H04M 1/725* | (2006.01) | |

(52) U.S. Cl.
CPC ............. *A63B71/0686* (2013.01); *G01S 19/19* (2013.01); *G06F 1/163* (2013.01); *G06F 1/1632* (2013.01); *G06F 1/1684* (2013.01); *G06F 3/002* (2013.01); *A63B 22/02* (2013.01); *A63B 22/0605* (2013.01); *A63B 22/0664* (2013.01); *A63B 69/06* (2013.01); *A63B 71/0622* (2013.01); *A63B 2024/0009* (2013.01); *A63B 2024/0012* (2013.01); *A63B 2024/0068* (2013.01); *A63B 2071/063* (2013.01); *A63B 2071/0625* (2013.01); *A63B 2071/0627* (2013.01); *A63B 2071/0663* (2013.01); *A63B 2220/40* (2013.01); *A63B 2220/62* (2013.01); *A63B 2225/20* (2013.01); *A63B 2225/50* (2013.01); *A63B 2230/06* (2013.01); *H04M 1/72527* (2013.01)

(56) References Cited

U.S. PATENT DOCUMENTS

| | | | |
|---|---|---|---|
| 4,674,743 A | | 6/1987 | Hirano |
| 5,749,372 A | | 5/1998 | Allen et al. |
| 6,312,363 B1 | | 11/2001 | Watterson et al. |
| 6,527,674 B1 | | 3/2003 | Clem |
| 6,716,139 B1 | | 4/2004 | Hosseinzadeh-Dolkhani et al. |
| 6,746,247 B2 | | 6/2004 | Barton |
| 6,837,827 B1 | * | 1/2005 | Lee ............... A63B 24/0021 482/3 |
| 6,853,955 B1 | | 2/2005 | Burrell et al. |
| 6,921,351 B1 | | 7/2005 | Hickman et al. |
| 7,085,678 B1 | | 8/2006 | Burrell et al. |
| 7,572,205 B1 | | 8/2009 | Cribar |
| 7,841,967 B1 | * | 11/2010 | Kahn ............... A63B 71/0686 482/8 |
| 2003/0040348 A1 | | 2/2003 | Martens |
| 2003/0171189 A1 | | 9/2003 | Kaufman |
| 2003/0224337 A1 | | 12/2003 | Shum et al. |
| 2005/0124463 A1 | | 6/2005 | Yeo et al. |
| 2005/0192156 A1 | | 9/2005 | Daikeler et al. |
| 2005/0209050 A1 | | 9/2005 | Bartels |
| 2005/0266961 A1 | | 12/2005 | Shum et al. |
| 2006/0004265 A1 | * | 1/2006 | Pulkkinen ............ A61B 5/0205 600/300 |
| 2006/0040793 A1 | * | 2/2006 | Martens ............ A63B 22/00 482/8 |
| 2006/0107822 A1 | | 5/2006 | Bowen |
| 2007/0011919 A1 | | 1/2007 | Case |
| 2007/0021269 A1 | | 1/2007 | Shum |
| 2007/0159926 A1 | | 7/2007 | Prstojevich et al. |
| 2007/0169614 A1 | | 7/2007 | Sasaki et al. |
| 2007/0260483 A1 | * | 11/2007 | Nurmela ............ A61B 5/0022 705/2 |
| 2007/0270663 A1 | | 11/2007 | Ng et al. |
| 2007/0271065 A1 | | 11/2007 | Gupta et al. |
| 2007/0271387 A1 | | 11/2007 | Lydon et al. |
| 2007/0271513 A1 | | 11/2007 | Andren |
| 2007/0287596 A1 | | 12/2007 | Case et al. |
| 2008/0096726 A1 | | 4/2008 | Riley et al. |
| 2008/0125288 A1 | | 5/2008 | Case |
| 2008/0153671 A1 | * | 6/2008 | Ogg ............... A63B 71/0686 482/3 |
| 2008/0188354 A1 | | 8/2008 | Pauws et al. |
| 2008/0254946 A1 | * | 10/2008 | Pauws ............ A63B 71/0686 482/8 |

FOREIGN PATENT DOCUMENTS

| | | |
|---|---|---|
| JP | 2004113552 A | 4/2004 |
| JP | 2005224318 A | 8/2005 |
| JP | 2006-251053 A | 9/2006 |
| JP | 2006239398 A | 9/2006 |
| JP | 2006259929 A | 9/2006 |
| JP | 2006263002 A | 10/2006 |
| JP | 2007033844 A | 2/2007 |
| JP | 2008524589 A | 7/2008 |
| WO | 02067449 A2 | 8/2002 |
| WO | 2004072767 A2 | 8/2004 |
| WO | 2005082472 A1 | 9/2005 |
| WO | 2006/085237 A1 | 8/2006 |
| WO | 2006085236 A2 | 8/2006 |

OTHER PUBLICATIONS

The Fourth Office Action for Chinese patent application No. 200810005936.8 mailed Apr. 2, 2013.
Decision of Rejection for Chinese patent application No. 200810005936.8 mailed Jul. 30, 2013.
Notice of Reasons for Rejection for Japanese patent application No. 2013-119514 mailed Nov. 27, 2013.
Notice of Reasons for Rejection for Japanese patent application no. 2013-119658 mailed Nov. 27, 2013.
European Office Action for patent application No. 08729984.8 mailed Mar. 4, 2014.
Office action received in related Chinese patent application No. 2008100059368 mailed Oct. 31, 2012.
The Second Office Action issued in corresponding Chinese Patent Application No. 200810005936.8 dated May 3, 2012.
Notice of Reasons for Rejection for Japanese patent application No. 2009-550151 mailed Apr. 9, 2012.
Office action for European application No. 08729984.8-2318 mailed Dec. 19, 2011.
Chinese Office Action for application No. 200810005936.8 mailed Sep. 30, 2011.
International Preliminary Report on Patentability received in connection with corresponding PCT Application No. PCT/US2008/054098 mailed Aug. 27, 2009.
Partial International Search Report received in connection with corresponding PCT Application No. PCT/US2008/054098 mailed Jul. 7, 2008.
International Search REport and Written Opinion received in connection with corresponding PCT Application No. PCT/US2008/054098 mailed on Sep. 29, 2008.

* cited by examiner

REAL-TIME COMPARISON OF ATHLETIC INFORMATION

RELATED APPLICATION DATA

This application is a continuation of and claims priority to co-pending U.S. patent application Ser. No. 12/031,941, filed Feb. 15, 2008 and entitled "Real-Time Comparison of Athletic Information," which claims priority benefits to U.S. Provisional Patent Appln. No. 60/890,223, filed Feb. 16, 2007, in the name of Roberto Tagliabue and entitled "Real-Time Comparison of Athletic Information." The priority applications are entirely incorporated herein by reference.

FIELD OF THE INVENTION

The present invention relates to the real-time comparison of athletic information. Some aspects of the invention have particular applicability to the generation of athletic data while a user is performing an athletic activity, comparing the athletic data with a baseline data, and providing feedback to the user while the user is still performing the athletic activity.

BACKGROUND OF THE INVENTION

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Experienced athletes and trainers have found that immediate and direct feedback provides many people with motivation to maximize the effort of their athletic activity. If a person is exercising with weights in gym, for example, a personal trainer will frequently provide that person words of encouragement, advice on lifting form, or other contemporaneous feedback. Unfortunately, it is often difficult to obtain direct feedback for some types of athletic activity, such as when a person is walking alone, running alone, riding a bicycle alone, or other solitary athletic activity away from sophisticated exercise equipment. Some manufacturers provide monitoring devices, such as heart rate monitors, pedometers, odometers and the like that a user can view while performing an athletic activity. While these monitoring devices do provide immediate feedback, they require the attention of the user, and thus may not provide feedback information when it might be of the most benefit to the user (e.g., as soon as the user begins to drop below or exceed a desired running pace).

In lieu of activity-specific or performance-specific feedback, many athletes listen to music or other audible content while performing an athletic activity. Some athletes, for example, believe that music or other audible content distracts their minds from monotonous athletic activities, such as walking, running, or bicycling. Accordingly, many athletes now use digital music players (i.e., players that play back music from a digital file stored on an electronic storage medium) to play back music during athletic activity sessions. With this type of music player, however, music or other audible content must be downloaded or otherwise transferred from an audible content file storage to the digital music player. In many cases, however, a user cannot accurately estimate how much audible content to transfer to the digital music player. The user may inadvertently transfer too little audible content to last for the entire duration of his or her planned athletic activity.

BRIEF SUMMARY OF THE INVENTION

Various aspects of the invention relate to the real-time comparison of athletic information with baseline data, in order to provide immediate feedback to a user. With some implementations of the invention, athletic information obtained from monitoring an athlete during an athletic activity is used to generate athletic data. The athletic data is then compared with baseline data. The baseline data may be idealized or actual. For example, the baseline data may be artificially created athletic data corresponding to an ideal target athletic performance desired by the user. Alternately, the baseline data may reflect the performance characteristics of an athletic activity session previously made by the user or some other person, such as a professional athlete, personal trainer, or competitor of the user.

If the athletic data is within a desired proximity of the baseline data, then default feedback is provided to the user. If, however, the athletic data is outside of the desired proximity of the baseline data, then alternate feedback is selected and provided to the user. Moreover, with some implementations of the invention, the feedback is part of a continuous playback of music, so that the user need not divert his or her attention to a monitoring device in order to realize a benefit from the feedback.

For example, the feedback may be music played back to the user while the user is running. Further, the baseline data may be a desired pace. If the athletic data generated by the user's athletic activity is within a desired proximity to the baseline data (e.g., within 10% of the baseline pace value), then the music played back to the user may be music from a default play list selected by the user. If, however, the athletic data values generated by the user's athletic activity are significantly lower than the corresponding baseline data values, alternate music with a faster beat may be played back to the user. Alternately or additionally, spoken encouragement or instructions may be provided to the user, to encourage the user to increase his or her athletic performance to match the desired baseline data. Similarly, if the athletic data values generated by the user's athletic activity are significantly higher than the corresponding baseline data values, a second set of alternate music with a slower beat may be played back to the user. Alternately or additionally, spoken encouragement or instructions may be provided to the user, to encourage the user to decrease his or her athletic performance to match the desired baseline data.

Various implementations of the invention may provide a digital music player for playing back music to a user while he or she is performing an athletic activity. With some of these implementations, a user may input a desired goal for an athletic activity session. For example, if a user is going to run, the user may input a desired distance for the run. In response to this input, an expected duration time for the athletic activity session is estimated. An amount of audible content corresponding to the expected duration time is then transferred from an audible content file storage to the digital music player for playback during the athletic activity session.

These and other features of the invention will become apparent from the following detailed description.

DETAILED DESCRIPTION OF THE INVENTION

Figure 1:
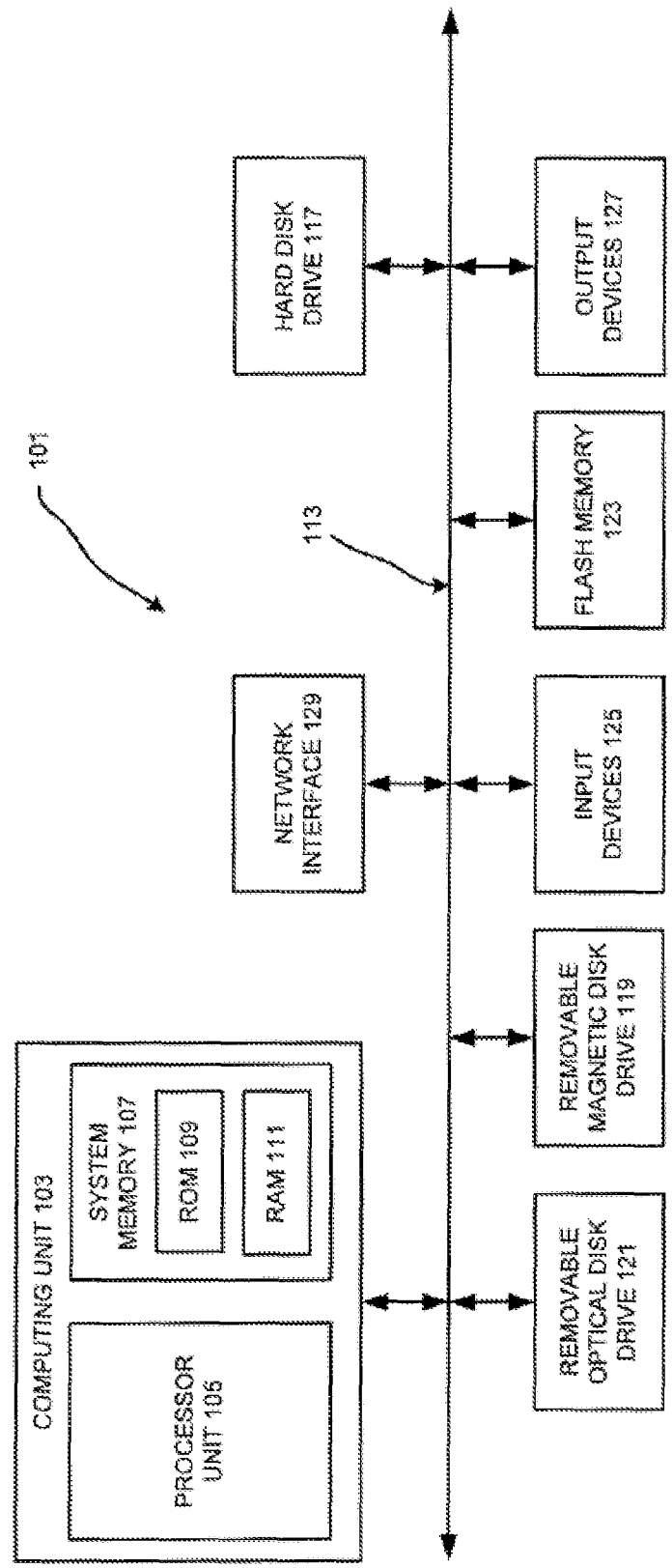
FIG. 1 illustrates a computing device that may be used to implement various examples of the invention.

Operating Environment
Overview

Aspects of the invention relate to the measurement, collection and display of athletic information. As will be appreciated by those of ordinary skill in the art, athletic information first must be obtained from an individual person. With various implementations of the invention, one or more different athletic information monitoring devices may be used to measure and record athletic information corresponding to athletic activity performed by a person during an athletic activity session. Typically, an athletic information monitoring device will incorporate a sensor for measuring parameters relating to the person being monitored and a computing device for processing the athletic information measured by the sensor into athletic data corresponding to the monitored athletic activity.

Once an athletic information monitoring device has recorded athletic information for a person's athletic activity, the person then may transfer the recorded athletic information to one or more separate devices, in order to view the recorded athletic information. A user may, for example, download generated and recorded athletic data from an athletic information monitoring device to a separate collection device. The collection device may, in turn, transfer the athletic data collected from the athletic information monitoring device to a separate display configuration device, where the athletic data can be organized and configured for subsequent viewing with, e.g., still another device. As will be discussed in more detail below, various implementations of the invention will allow a person to record, collect and display athletic information using a group of computing devices communicating over a network, such as the Internet.

For example, some implementations of the invention may allow a person to measure and record athletic information using a special-purpose computing device. The user then can transfer athletic data generated from the athletic information to a local computing device, such as a personal desktop or laptop computer. More particularly, a user can download recorded athletic data from the athletic information monitoring device to a collection software tool on a local computer that acts as a "client" in a computer network. The collection software tool then will transfer the downloaded athletic data through the network to a remote "server" computer. A display configuration software tool on the remote server computer then will save the transferred athletic data. Later, a person can use the client computer or another local computer to retrieve the stored athletic data from the server computer. In response to a display request from a local computer, the display configuration software tool will configure the requested athletic data for display on the local computer, and then transmit the configured athletic data to the local computer for display.

Computing Device

Various examples of the invention may be implemented using electronic circuitry configured to perform one or more functions. For example, with some embodiments of the invention, the athletic information monitoring device, the collection device, the display device or any combination thereof may be implemented using one or more application-specific integrated circuits (ASICs). More typically, however, one or more components of various examples of the invention will be implemented using a programmable computing device executing firmware or software instructions, or by some combination of purpose-specific electronic circuitry and firmware or software instructions executing on a programmable computing device.

Accordingly, FIG. 1 shows one illustrative example of a computer 101 that can be used to implement various embodiments of the invention. As seen in this figure, the computer 101 has a computing unit 103. The computing unit 103 typically includes a processing unit 105 and a system memory 107. The processing unit 105 may be any type of processing device for executing software instructions, but it will conventionally be a microprocessor device. The system memory 107 may include both a read-only memory (ROM) 109 and a random access memory (RAM) 111. As will be appreciated by those of ordinary skill in the art, both the read-only memory (ROM) 109 and the random access memory (RAM) 111 may store software instructions for execution by the processing unit 105.

The processing unit 105 and the system memory 107 are connected, either directly or indirectly, through a bus 113 or alternate communication structure to one or more peripheral devices. For example, the processing unit 105 or the system memory 107 may be directly or indirectly connected to additional memory storage, such as the hard disk drive 117, the removable magnetic disk drive 119, the removable optical disk drive 121, and the flash memory card 123. The processing unit 105 and the system memory 107 also may be directly or indirectly connected to one or more input devices 125 and one or more output devices 127. The input devices 125 may include, for example, a keyboard, touch screen, a remote control pad, a pointing device (such as a mouse, touchpad, stylus, trackball, or joystick), a scanner, a camera or a microphone. The output devices 127 may include, for example, a monitor display, television, printer, stereo, or speakers.

Still further, the computing unit 103 will be directly or indirectly connected to one or more network interfaces 129 for communicating with a network. This type of network interface 129, also sometimes referred to as a "network adapter" or "network interface card" ("NIC"), translates data and control signals from the computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 129 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player available from Apple, Inc. of Cupertino, Calif. As known in the art, this type of digital music player can serve as both an output device for a computer (e.g., outputting music from a sound file or pictures from an image file) and a storage device. In addition, this type of digital music player also can serve as an input device for inputting recorded athletic information, as will be discussed in more detail below.

Of course, still other peripheral devices may be included with or otherwise connected to a computer 101 of the type illustrated in FIG. 1, as is well known in the art. In some cases, a peripheral device may be permanently or semi-permanently connected to the computing unit 103. For example, with many computers, the computing unit 103, the hard disk drive 117, the removable optical disk drive 121 and a display are semi-permanently encased in a single housing. Still other peripheral devices may be removably connected to the computer 101, if desired. The computer 101 may include, for example, one or more communication ports through which a peripheral device can be connected to the computing unit 103 (either directly or indirectly through the bus 113). These communication ports may include a parallel bus port or a serial bus port, such as a serial bus port using the Universal Serial Bus (USB) standard or the IEEE 1394 High Speed Serial Bus standard (e.g., a Firewire port). Alternately or additionally, the computer 101 may include a wireless data "port," such as a Bluetooth interface, a Wi-Fi interface, an infrared data port, or the like.

It should be appreciated that a computing device employed according various examples of the invention may include more components than the computer 101 illustrated in FIG. 1, fewer components than the computer 101, or a different combination of components than the computer 101. Some implementations of the invention, for example, may employ one or more computing devices that are intended to have a very specific functionality, such as a digital music player or server computer. These computing devices may thus omit unnecessary peripherals, such as the network interface 129, removable optical disk drive 121, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Athletic Information Monitoring Device

Figure 2:
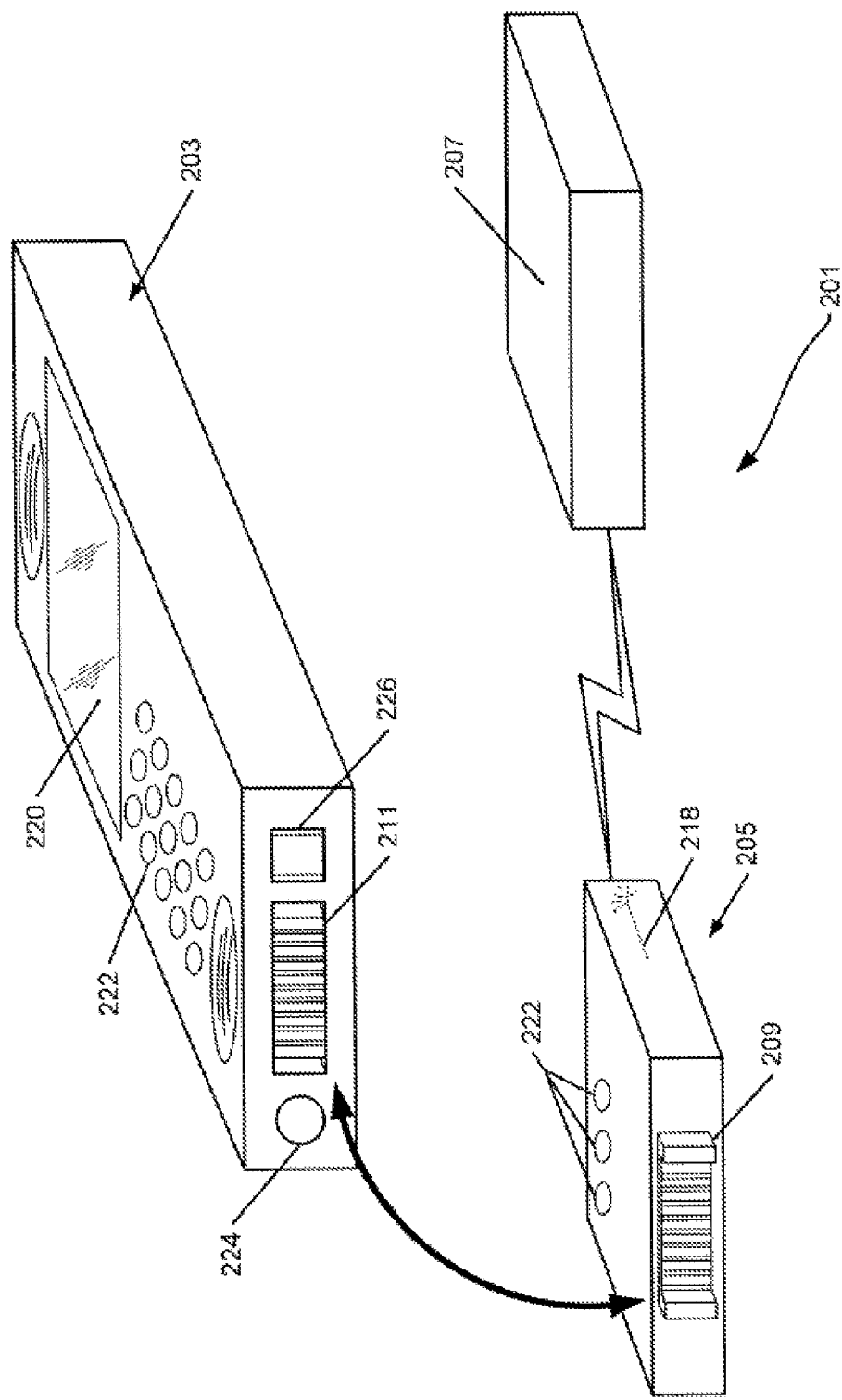
FIGS. 2 and 3 illustrate an example of an athletic information monitoring device that may be employed according to various examples of the invention.

FIG. 2 illustrates one example of an athletic information monitoring device 201 that may be employed according to various examples of the invention to measure athletic information corresponding a user's athletic activity. As shown in this figure, the athletic information monitoring device 201 includes a digital music player 203, an electronic interface device 205, and an athletic parameter measurement device 207. As will be described in more detail below, the digital music player 203 is (releasably) connected to the electronic interface device 205, and the combination is worn or otherwise carried by the user while he or she is performing an athletic activity, such as running or walking. The athletic parameter measurement device 207 also is worn or carried by the user while he or she is performing an athletic activity, and this device 207 measures one or more athletic parameters relating to the athletic performance being performed by the user. The athletic parameter measurement device 207 transmits signals to the electronic interface device 205 that correspond to the measured athletic parameter.

The electronic interface device 205 receives the signals from the athletic parameter measurement device 207, and it provides the athletic information carried by the signals to the digital music player 203. The electronic interface device 205 includes a connector system 209 that physically plugs into and connects with a conventional input port 211 provided on digital music player 203. The input port 211 into which the connector system 209 of the electronic interface device 205 connects may be any desired type of input port for transferring data, such as a parallel data port, a serial data port, an earphone or microphone jack, etc. The connector system 209 may include any suitable connecting devices, such as wires, pins, electrical connectors, and the like, so as to make an electrical connection or other suitable connection with corresponding elements provided in the input port 211 of the digital music player 203 (e.g., to allow electronic and/or data communications between the interface device 205 and the digital music player device 203). If necessary or desired, additional securing elements may be provided to securely connect the interface device 205 to the digital music player 203, such as straps, hooks, buckles, clips, clamps, clasps, retaining elements, mechanical connectors, and the like.

Figure 3:
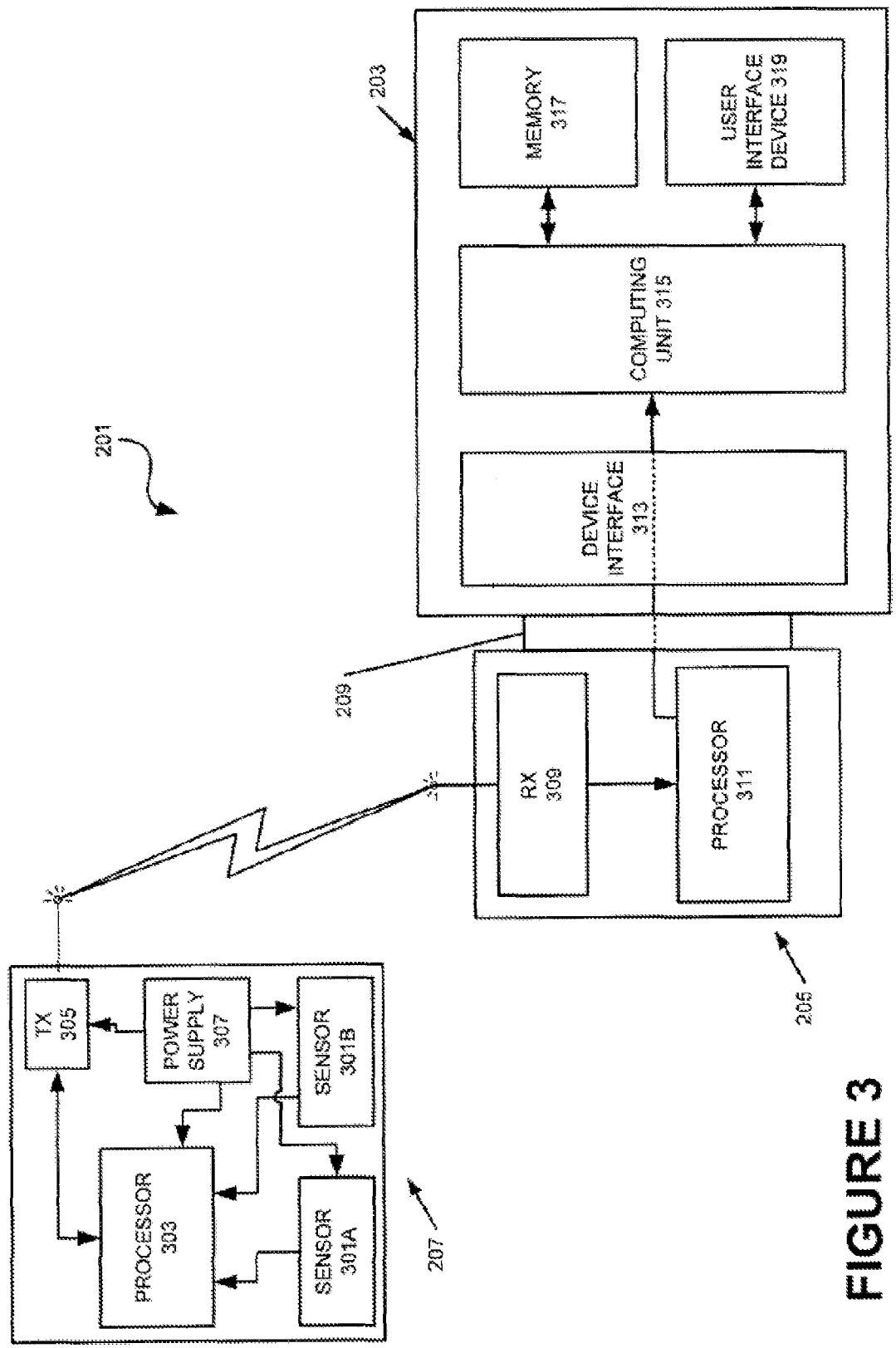
Figure 4:
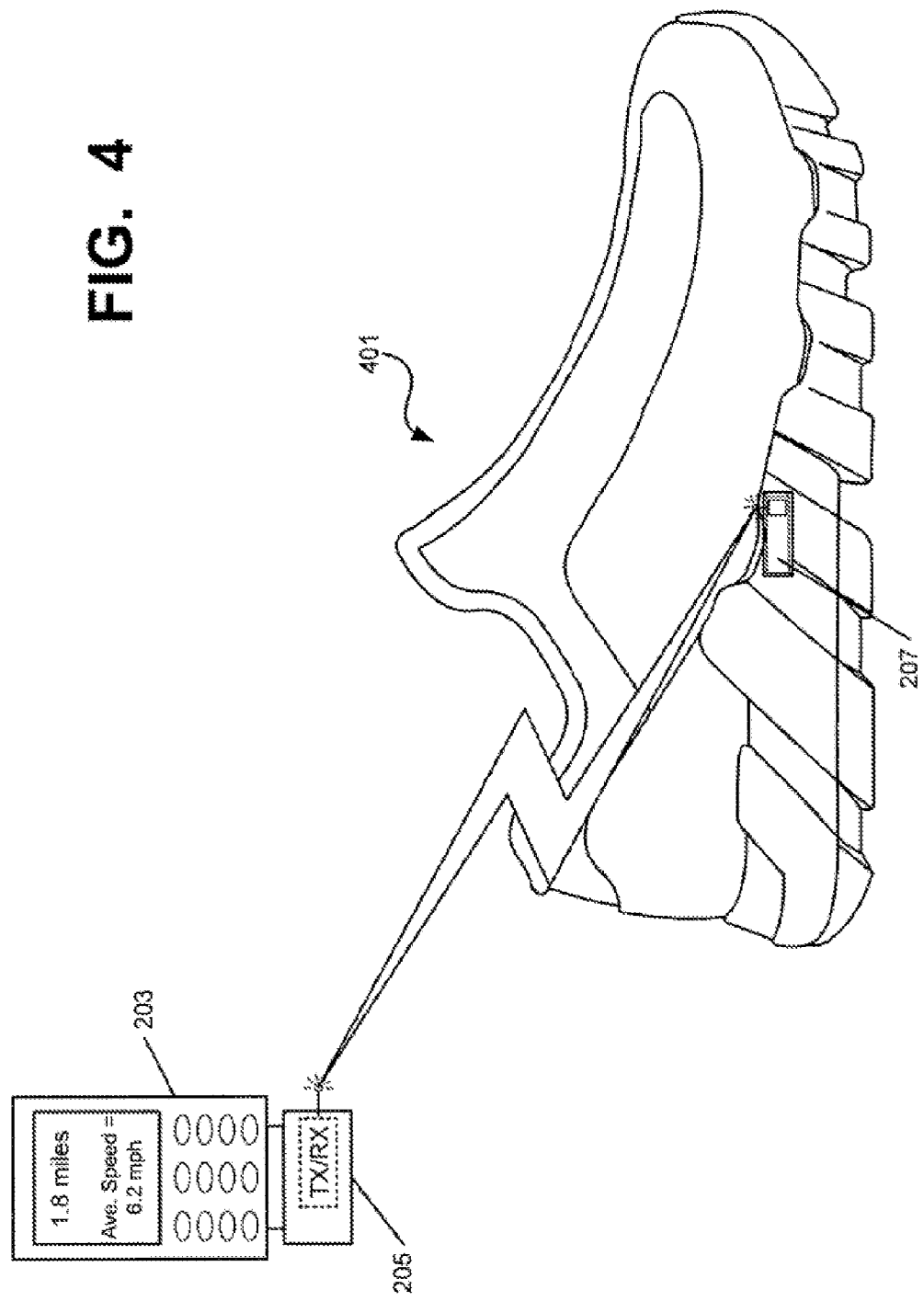
FIG. 4 illustrates one environment in which an athletic parameter measurement device according to various examples of the invention may be employed.

As shown in more detail in FIG. 3, the athletic parameter measurement device 207 includes one or more sensors 301 for measuring an athletic parameter associated with a person wearing or otherwise using the athletic parameter measurement device 207. With the illustrated implementations, for example, the sensors 301A and 301B may be accelerometers (such as piezoelectric accelerometers) for measuring the acceleration of the athletic parameter measurement device 207 in two orthogonal directions. The athletic parameter measurement device 207 is carried or otherwise worn by a user, so that it measures the desired athletic parameter while the user exercises. For example, as shown in FIG. 4, the athletic parameter measurement device 207 may be located in the sole of a user's shoe 401 while the user walks or runs. With this arrangement, the sensors 301 will produce electrical signals corresponding to the movement of the user's foot. As known in the art, these signals can then be used to generate athletic data representative of the athletic activity performed by the user.

The athletic parameter measurement device 207 also includes a processor 303 for processing the electrical signals output by the sensors 301. With some implementations of the invention, the processor 303 may be a programmable microprocessor. For still other implementations of the invention, however, the processor 303 may be a purpose-specific electronic circuit device, such as an ASIC. The processor 303 may perform any desired operation on the signals output from the sensors 301, such as curve smoothing, noise filtering, outlier removal, amplification, summation, integration, or the like. The processor 303 provides the processed signals to a transmitter 305. The athletic parameter measurement device 207 also includes a power supply 307, for providing power to the sensors 301, the processor 303, and the transmitter 305 as needed. The power supply 307 may be, for example, a battery.

The athletic parameter measurement device 207 transmits the processed signals to the electronic interface device 205, as seen in FIG. 4. Returning now to FIG. 3, the electronic interface device 205 includes a receiver 309 which receives the processed signals transmitted by the transmitter 305 in the athletic parameter measurement device 207. The receiver 309 relays the processed signals to a second processor 311, which processes the signals further. Like the processor 303, the processor 311 may perform any desired operation on the processed signals, such as curve smoothing, noise filtering, outlier removal, amplification, summation, integration, or the like.

The processor 311 provides the processed signals to the computing unit 315 through a device interface 313. With various examples of the invention, the device interface 313 may physically incorporate, e.g., the input port 211. It also may employ electrical components, software components (such as application program interfaces (APIs)), or some combination thereof. The computing unit 315 may initially store the information carried by the processed signals in the memory 317. Also, the computing unit 315 may receive input from and provide output to a user through a user interface 319. The user interface 319 may include any type of user interface devices, include, e.g., display screens, touchpads, keyboards, joysticks, trackballs and the like.

With various implementations of the invention, the computing unit 315 operates on the processed signals provided by the athletic information monitoring device 201 to generate a set of athletic data corresponding to the athletic activity performed by the user. For example, if the athletic information monitoring device 201 includes accelerometers for measuring the movement of the user's foot, the computing unit 315 may analyze the processed signals from the athletic information monitoring device 201 to generate sets of athletic data describing, e.g., the user's speed at specific instances during the user's athletic activity and the total distance traveled by the user at each of those specific instances. Various techniques for determining athletic data from accelerometer signals are described in, for example, U.S. Pat. No. 6,898,550 to Blackadar et al., entitled "Monitoring Activity Of A User In Locomotion On Foot," and issued on May 24, 2005; U.S. Pat. No. 6,882,955 to Ohlenbusch et al., entitled "Monitoring Activity Of A User In Locomotion On Foot," and issued on Apr. 19, 2005; U.S. Pat. No. 6,876,947 to Darley et al., entitled "Monitoring Activity Of A User In Locomotion On Foot," and issued on Apr. 5, 2005; U.S. Pat. No. 6,493,652 to Ohlenbusch et al., entitled "Monitoring Activity Of A User In Locomotion On Foot," and issued on Dec. 10, 2002; U.S. Pat. No. 6,298,314 to Blackadar et al., entitled "Detecting The Starting And Stopping Of Movement Of A Person On Foot," and issued on Oct. 2, 2001; U.S. Pat. No. 6,052,654 to Gaudet et al., entitled "Measuring Foot Contact Time And Foot Loft Time Of A Person In Locomotion," and issued on Apr. 18, 2000; and U.S. Pat. No. 6,018,705 to Gaudet et al., entitled "Measuring Foot Contact Time And Foot Loft Time Of A Person In Locomotion," and issued on Jan. 25, 2000; each of which is incorporated entirely herein by reference.

Each athletic data set may also include a time value associated with each speed value and/or each distance value. If the athletic information monitoring device 201 can be employed to collect athletic information from different users, then the computing unit 315 may additionally prompt the user to identify himself or herself in some way. This identification information may then be included or otherwise associated with each athletic data set generated from the information provided by the athletic information monitoring device 201. Once the computing unit 315 has generated a set of athletic data from the information provided by the athletic information monitoring device 201, the computing unit 315 may store the athletic data set in the memory 317. As will be discussed in more detail below, when the digital music player 203 subsequently is connected to a computing device implementing an athletic information collection tool, the computing unit 315 will download the athletic data to the collection tool.

While wireless communication between the athletic parameter measurement device 207 and the interface device 205 is described for the embodiments illustrated in FIGS. 2-4, any desired manner of communicating between the athletic parameter measurement device 207 and the interface device 205 may be used without departing from the invention, including wired connections. Also, any desired way of placing data derived from the physical or physiological data from the athletic parameter measurement device 207 in the proper form or format for display on or output from digital music player 203 may be provided without departing from the invention. For example, if desired, the athletic parameter measurement device 207 may be specially designed and/or programmed for use with one or more specific digital music players 203 or other electronic devices, e.g., pre-programmed and/or wired to operate with a specific device or devices 203 and to provide output data in a form and format suitable for those devices 203. In this situation, the interface devices 205 may be marketed and sold to specifically target certain electronic devices 203, such as specific models of digital music players and even other electronic devices, such as telephones, watches, personal digital assistants, etc. As another alternative, if desired, the interface devices 205 may be programmed at a later time to operate with a wide variety of different electronic devices, e.g., by downloading display or device driver and/or format data for specific electronic devices from the Internet, from disk, or from another source, etc.

If desired, in accordance with at least some examples of this invention, the electronic interface device 205 and/or the digital music player 203 may further include a display 220 and/or a user input system 222, such as one or more rotary input devices, switches, buttons (as shown in the illustrated example in FIG. 2), mouse or trackball elements, touch screens, or the like, or some combination thereof. The display 220 may be employed to show, for example, information relating to music being played by the digital music player 203, information relating to the athletic information signals being received by the digital music player 203, athletic data being generated by the digital music player 203 from the received athletic information signals, etc. The user input system 222 may be employed, for example: to control one or more aspects of the processing of the input data received via interface device 205, to control input data receipt (e.g., timing, types of information received, on-demand data requests, etc.), to control data output to or by the electronic device 203, to control the athletic parameter measurement device 207, etc. Alternatively or additionally, if desired, the input system on the digital music player 203 (e.g., buttons 222, a touch screen, a digitizer/stylus based input, a rotary input device, a trackball or roller ball, a mouse, etc.), may be used to provide user input data to the interface device 205 and/or to the athletic parameter measurement device 207. As still another example, if desired, a voice input system may be provided with the interface device 205 and/or the digital music player 203, e.g., to enable user input via voice commands. Any other desired type of user input system, for control of any system elements and/or for any purpose, may be provided without departing from the invention.

The digital music player 203 may include additional input and/or output elements, e.g., such as ports 224 and 226 shown in FIG. 2, e.g., for headphones (or other audio output), power supplies, wireless communications, infrared input, microphone input, or other devices. If desired, and if these ports 224 and/or 226 would be covered when the interface device 205 is attached to the electronic device 203, the interface device 205 may be equipped with similar external ports to ports 224 and/or 226, and internal circuitry may be provided in the interface device 205 to enable the user to plug the same additional devices into the interface device 205 as they might plug into the digital music player 203 and still take advantage of the same functions (e.g., to thereby allow the necessary data, signals, power, and/or information to pass through the interface device 205 to the user, to another output, and/or to the digital music player 203).

It should be appreciated that, while some specific embodiments of the invention described above relate to a digital music player 203, alternate examples of the invention may be implemented using any portable electronic device. For example, with some implementations of the invention, the athletic parameter measurement device 207 may be used in conjunction with a mobile telephone, a watch, a personal digital assistant, another type of music player (such as a compact disc or satellite radio music player), a portable computer, or any other desired electronic device. Still further, some implementations of the invention may alternately or additionally omit the use of the interface device 205. For example, the athletic parameter measurement device 207 may be configured to communicate using the Bluetooth wireless communication protocol, so that it can be employed with Bluetooth-capable mobile telephones, personal digital assistants, watches or personal computers. Of course, still other wireless or wired communication techniques could be employed while omitting the interface device 205.

It also should be appreciated that, while a specific example of an athletic parameter measurement device 207 has been described above for ease of understanding, any type of desired athletic parameter measurement device 207 can be employed with various embodiments of the invention. For example, with some implementations of the invention, the athletic parameter measurement device 207 may be a heart rate monitor, a blood oxygen monitor, a satellite positioning device (e.g., a Global Positioning Satellite (GPS) navigation device), a device for measuring the electrical activity of the user (e.g., an EKG monitor), or any other device that measures one or more physical parameters of the user. Still further, the athletic parameter measurement device 207 may measure one or more operational parameters of some device being manipulated by the user, such as the speed and/or distance of a bicycle; the speed and/or work performed by a treadmill, rowing machine, elliptical machine, stationary bicycle, or the like; the speed and/or distance traveled by skis (water or snow), skates (roller or ice), or snowshoes or the like worn by the user; etc.

Also, while the athletic parameter measurement device 207 has been described as being separate from the digital music player 203, with some implementations of the invention the athletic parameter measurement device 207 may be incorporated into the digital music player 203 or another electronic device. For example, some implementations of the invention may employ a music player, mobile telephone, watch or personal digital assistant that incorporates accelerometers, a satellite positioning device, or any other desired device for measuring some parameter of athletic activity. Still further, it should be appreciated that various implementations of the invention may employ a plurality of athletic parameter measurement devices 207, incorporated into the digital music player 203 or other portable electronic device, separate from the digital music player 203, or some combination thereof.

Feedback Control Tools

Figure 5:
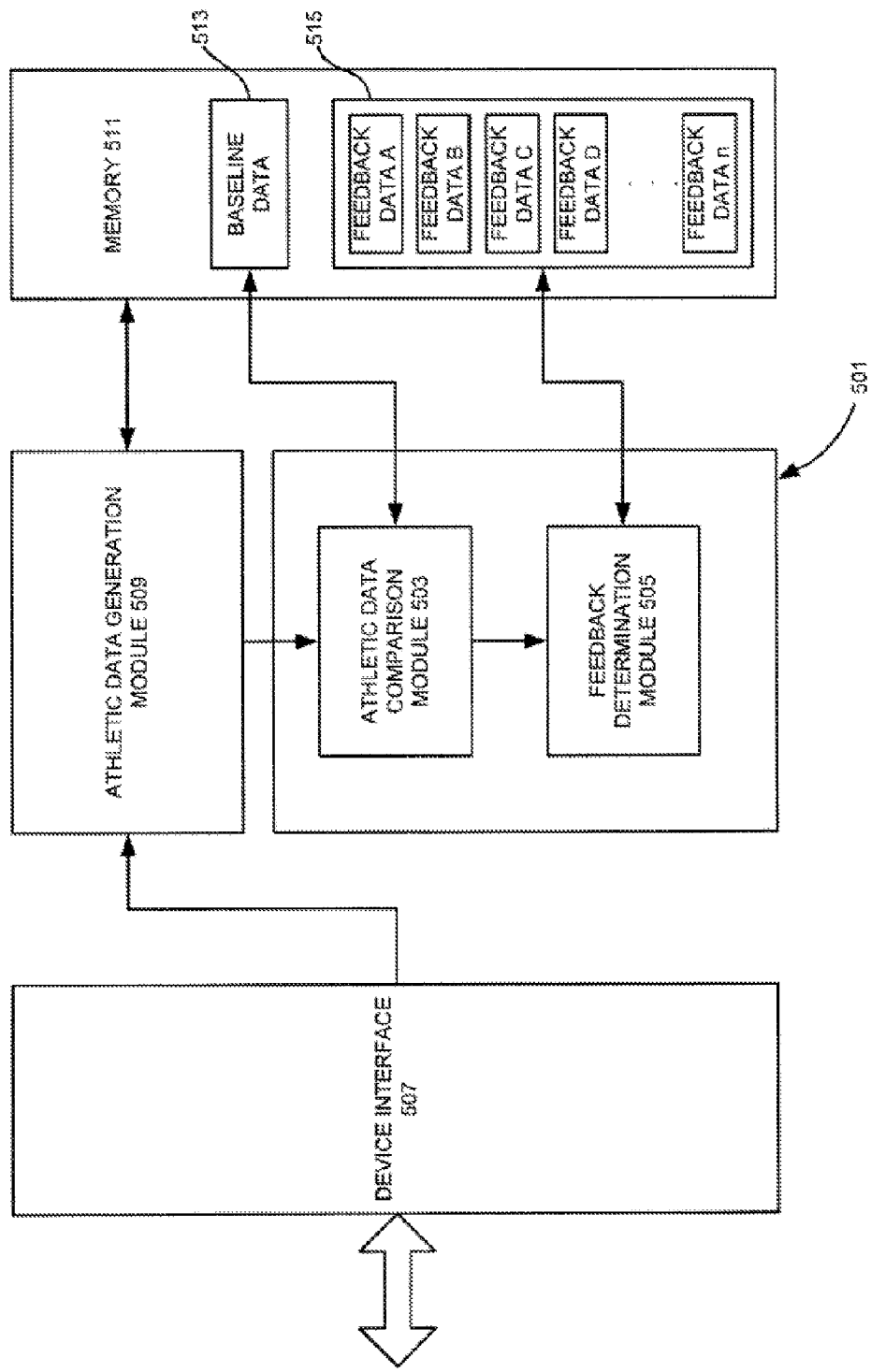
FIG. 5 illustrates an example of a feedback control tool that may be employed to control the feedback provided to a user during an athletic activity session according to various examples of the invention.

FIG. 5 illustrates an example of feedback control tool 501 that may be employed to control the feedback provided to a user during an athletic activity session. As shown in this figure, the feedback control tool 501 includes an athletic data comparison module 503, and a feedback determination module 505. As will be discussed in more detail below, the feedback control tool 501 may be implemented in, e.g., a digital music player that also includes a device interface 507, an athletic data generation module 509, and a memory 511. Each of the athletic data comparison module 503, the feedback determination module 505 and the athletic data generation module 509 may be implemented by, for example, software instructions executed by a computing unit 103 of a computing device 101.

The device interface 507 receives athletic information from the athletic information monitoring device 201. The device interface 507 may be implemented by, e.g., a device interface 313 of the type previously discussed, using, e.g., electrical components, software components (such as application program interfaces (APIs)), or some combination thereof.

The athletic data generation module 509, which may be implemented using a computing unit 315 as previously discussed, operates on signals provided by an athletic information monitoring device 201 to generate a set of athletic data corresponding to the athletic activity performed by the user. For example, if the athletic information monitoring device 201 includes accelerometers for measuring the movement of the user's foot, the athletic data generation module 509 may analyze the processed signals from the athletic information monitoring device 201 to generate sets of athletic data describing, e.g., the user's speed at specific instances during the user's athletic activity and the total distance traveled by the user at each of those specific instances. Various techniques for determining athletic data from accelerometer signals are described in, for example, U.S. Pat. No. 6,898,550 to Blackadar et al., entitled "Monitoring Activity Of A User In Locomotion On Foot," and issued on May 24, 2005; U.S. Pat. No. 6,882,955 to Ohlenbusch et al., entitled "Monitoring Activity Of A User In Locomotion On Foot," and issued on Apr. 19, 2005; U.S. Pat. No. 6,876,947 to Darley et al., entitled "Monitoring Activity Of A User In Locomotion On Foot," and issued on Apr. 5, 2005; U.S. Pat. No. 6,493,652 to Ohlenbusch et al., entitled "Monitoring Activity Of A User In Locomotion On Foot," and issued on Dec. 10, 2002; U.S. Pat. No. 6,298,314 to Blackadar et al., entitled "Detecting The Starting And Stopping Of Movement Of A Person On Foot," and issued on Oct. 2, 2001; U.S. Pat. No. 6,052,654 to Gaudet et al., entitled "Measuring Foot Contact Time And Foot Loft Time Of A Person In Locomotion," and issued on Apr. 18, 2000; and U.S. Pat. No. 6,018,705 to Gaudet et al., entitled "Measuring Foot Contact Time And Foot Loft Time Of A Person In Locomotion," and issued on Jan. 25, 2000, each of which is incorporated entirely herein by reference.

Figure 6A:
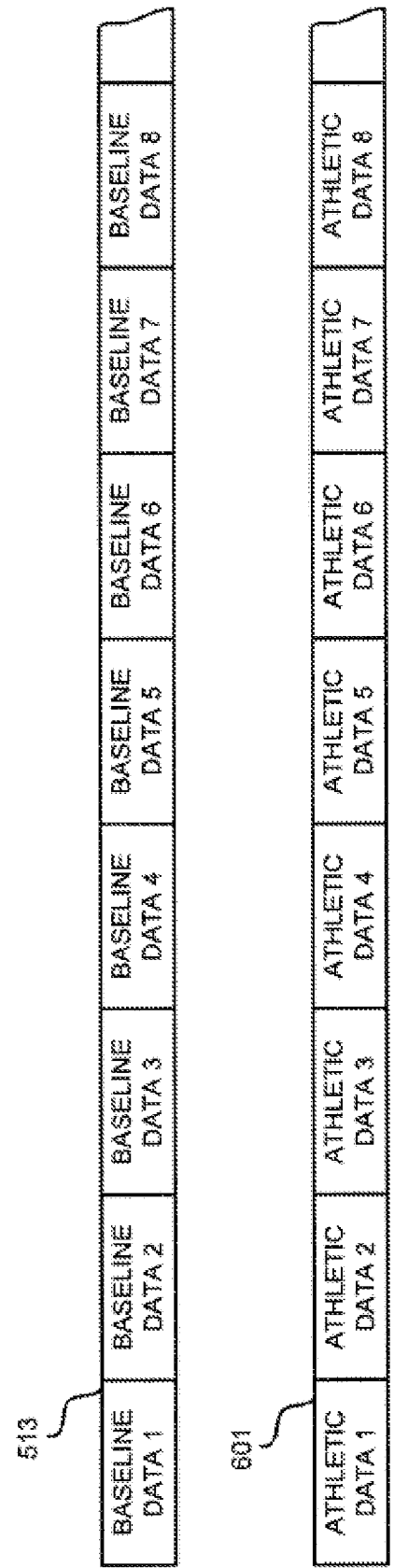
FIGS. 6A and 6B illustrate types of data that may be employed by a feedback control tool according to various examples of the invention.

The memory 511 (which may be implemented using a memory 317 of the type discussed in detail above) may store athletic data sets generated by the athletic data generation module 509. With various examples of the invention, however, the memory 511 also includes baseline data 513 and a plurality of groups of feedback data 515. The baseline data 513 typically will have one or more data values corresponding to the athletic data values generated by the athletic data generation module 509. For example, turning to FIG. 6A, the athletic data 601 generated by the athletic data generation module 509 will include a series of data sets (e.g., athletic data 1, athletic data 2, athletic data 3, athletic data 4 . . . athletic data n) at various times during the user's athletic activity session. Each data set will include at least one data value, such as a pace or distance value. The baseline data 513 similarly includes a series of data sets (e.g., baseline data 1, baseline data 2, baseline data 3, baseline data 4 . . . baseline data n) corresponding to the athletic data sets generated by the athletic data generation module 509. As will be discussed in more detail below, the baseline data 513 can be played back by the digital music player 203 along with, e.g., feedback in the form of audible content while the user is performing an athletic activity for comparison with the athletic data 601 generated by the athletic data generation module 509.

It should be noted that the baseline data 513 may be any data desired by the user. For example, the baseline data 513 may be athletic data 601 created during a previously completed athletic activity session. This arrangement allows a user to, for example, employ the results of a particularly successful athletic activity session as a baseline to which future athletic activity sessions should be compared to determine the user's performance improvement. Various implementations of the invention may alternately or additionally allow a user to manually create the baseline data 513. This arrangement allows a user to, for example, create an ideal performance standard for athletic activity sessions. Still further, some implementations of the invention may alternately or additionally allow a user to employ athletic data generated by another person as the baseline data 513. This arrangement allows the user to compare his or her athletic activity performance with, e.g., a professional athlete, a personal trainer, a competitor or the like.

It should be appreciated that, like the athletic data 601, the values of the baseline data 513 may change over time. For example, the baseline data 513 may include a relatively slow pace value for early in the athletic activity session, with a higher pace value for the middle of the athletic activity session. The baseline data 513 can then return to lower pace values (or other desired pace values) for the end of the activity session.

Figure 6B:
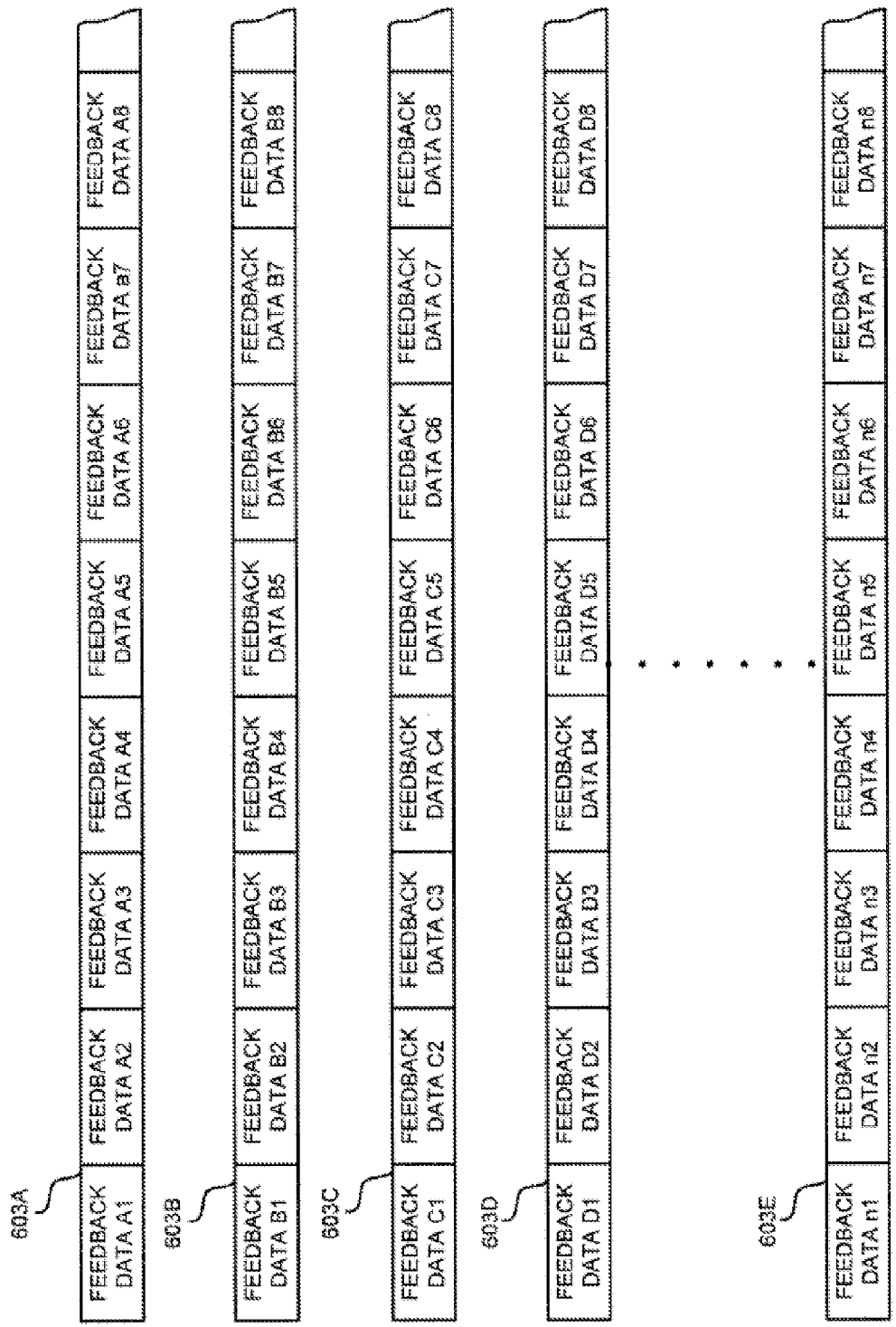

As previously noted, the memory 511 may include a plurality of groups of feedback data 515. As shown in FIG. 6B, each group 603 of feedback data 515 may include a series of feedback data values that can be played back by the digital music player 203 to the user. Typically, a group 603 of feedback data 515 will be audible content, such as music or spoken content. With some implementations of the invention, however, a group 603 of feedback data 515 may alternately or additionally include visual content or tangible content (e.g., signal to provide a mild electrical shock or vibrational response to the user).

The feedback data 515 typically will include a feedback data group 603 representing a default feedback for the user during an athletic activity session. This default feedback data group 603 may be, for example, a music playlist selected by the user of preferred music. The feedback data 515 also may include one or more alternate feedback data groups 603. These alternate feedback data groups 603 have values that are configured to influence the performance of the user's athletic activity relative to the default feedback data group 603. For example, one alternate feedback data group 603 may be music that has a 10% faster rhythm than the music of the default feedback data group 603. A second alternate feedback data group 603 may have a 20% faster rhythm than the music of the default feedback data group 603, while a third alternate feedback data group 603 may be music that has a 10% slower rhythm than the music of the default feedback data group 603 and a fourth alternate feedback data group 603 may have a 20% slower rhythm than the music of the default feedback data group 603. Alternately or additionally, the alternate feedback groups 603 may include spoken content designed to influence the athletic performance of the user, such as words of encouragement or performance instructions.

Figure 7:
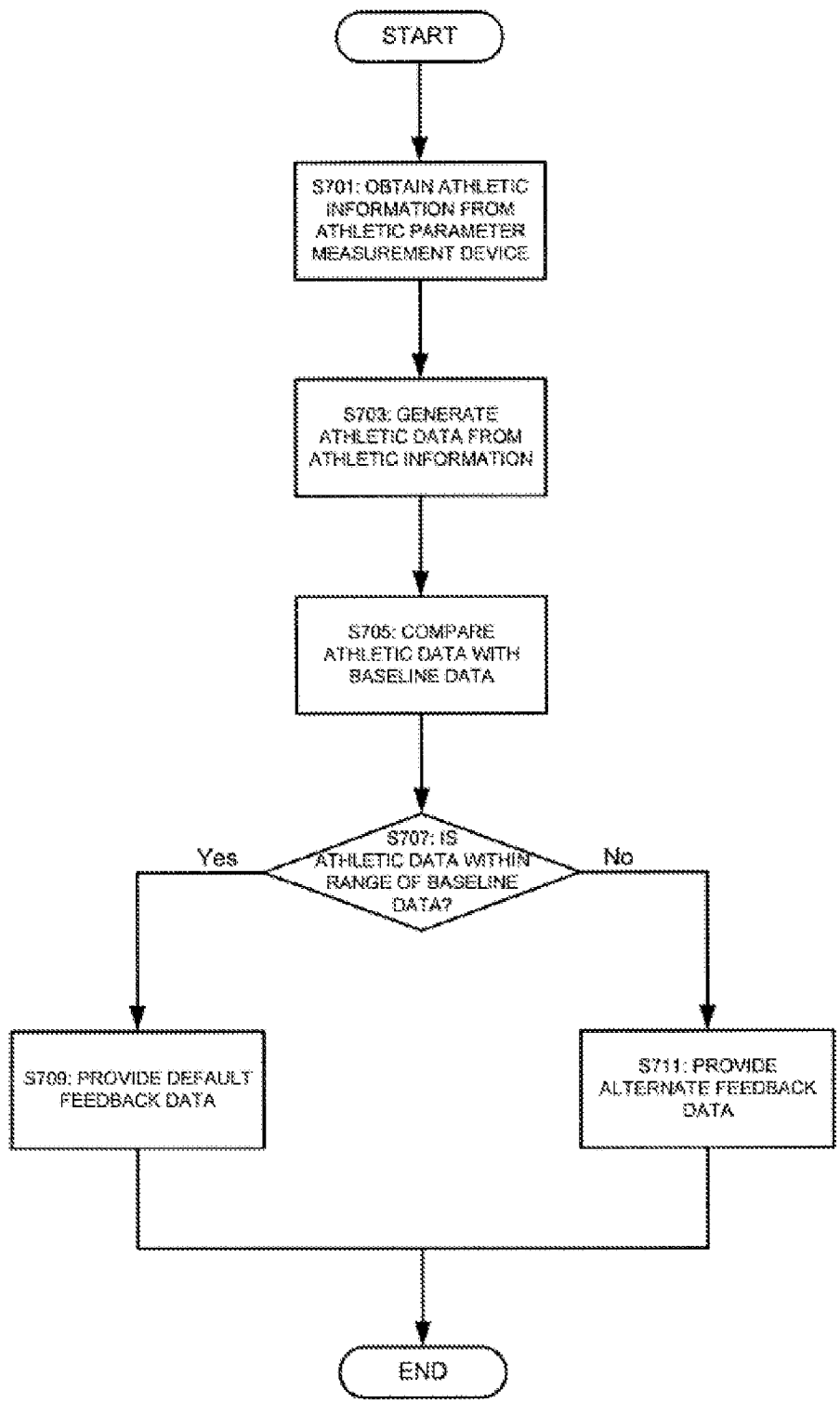
FIG. 7 illustrates a flowchart describing a method of providing real-time feedback to a user during an athletic activity session according to various examples of the invention.

The operation of the feedback control tool 501 now will be discussed with regard to FIG. 7. Initially, in step 701, the athletic data generation module 509 obtains athletic information from the athletic parameter measurement device 207.

Next, in step 703, the athletic data generation module 509 generates athletic data from the received athletic information as discussed in detail above. After the athletic data has been generated by the athletic data generation module 509, the athletic data comparison module 503 retrieves the baseline data 513 from the memory 511, and compares the retrieved baseline data 513 with the generated athletic data 601 in step 705.

Next, in step 707 the athletic data comparison module 503 determines whether each value of the athletic data 601 is within a desired proximity to the corresponding value of the baseline data 513. This desired proximity can be determined using any suitable or desired standard of measurement, including, e.g., by percentage or by a specific numerical values. For example, a particularly baseline data value may be a pace of 1 mile per 12 minutes. With some implementations of the invention, a corresponding measured athletic activity value may be outside of the desired proximity if it is below 10% of this pace. With still other implementations of the invention, however, a corresponding athletic activity value may be outside of the desired proximity if it is below 1 mile per 16 minutes.

It also should be noted that the range of desired proximity may vary between athletic data values above the corresponding baseline data value and athletic data values below the corresponding baseline data value. For example, a lower athletic data value may be outside of the desired proximity of the corresponding baseline data value if it is only 5% or more below the baseline data value, but a higher athletic data value may not be outside of the proximity of the corresponding baseline data value unless it is more than 10% above the baseline data value.

Next, the feedback determination module 505 selects the group 603 of feedback data 515 that will be provided to the user based upon the comparison results determined by the athletic data comparison module 503. For example, if the athletic data comparison module 503 has determined that the current athletic data value is within the desired proximity of its corresponding baseline data value, then the feedback determination module 505 will select the default group 603 of feedback data 515 in step 709. On the other hand, if the athletic data comparison module 503 has determined that the current athletic data value is outside of the desired proximity of its corresponding baseline data value, then the feedback determination module 505 will select an alternate group 603 of feedback data 515 in step 711.

With various examples of the invention, the feedback determination module 505 may determine an alternate feedback data group 603 based, at least in part, on the degree to which the measured athletic data value deviated from its corresponding baseline data value. For example, if the athletic data value is a pace that was approximately 10% slower than the baseline data value, then the feedback determination module 505 may select a feedback data group 603 that will play back music with a rhythm 10% faster than the default feedback data group 603. Similarly, if the athletic data value is a pace that was approximately 20% slower than the baseline data value, then the feedback determination module 505 may select a feedback data group 603 that will play back music with a rhythm 20% faster than the default feedback data group 603. Alternately or additionally, the feedback determination module 505 may select a feedback data group 603 that will play back spoken content strongly encouraging the user to increase his or her pace.

In this manner, various implementations of the invention provide a user with immediate feedback when he or she deviates from a desired baseline athletic performance. Moreover, the feedback can be provided on a continuous basis without requiring the specific attention of the user during the athletic activity.

Automatic Selection Of Feedback

Figure 8:
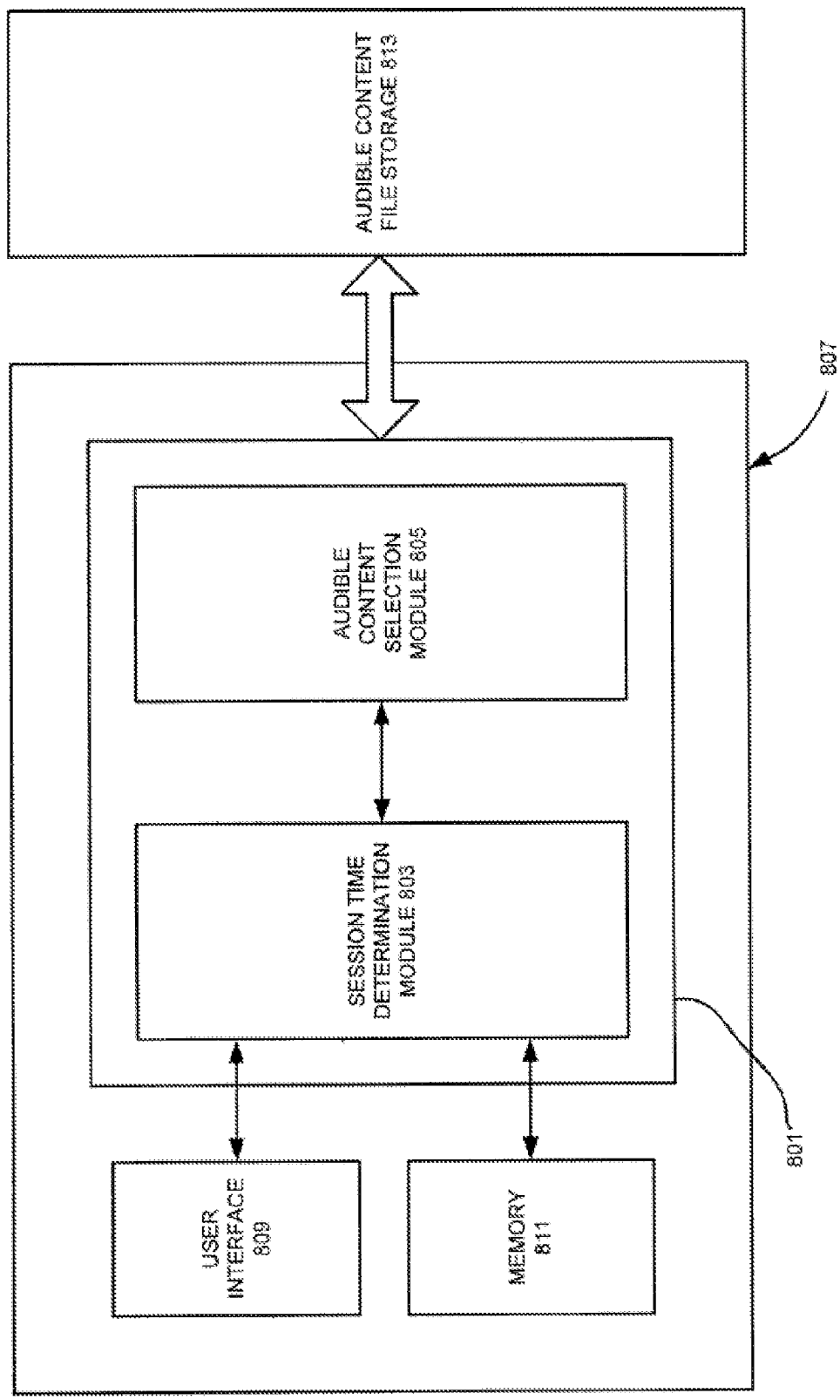
FIG. 8 illustrates an automatic feedback selection tool that may be employed according to various embodiments of the invention.

As will be discussed in more detail below, various examples of the invention may alternately or additionally assist a user by automatically selecting the amount of feedback data that will be provided to the user during an athletic activity session. Referring now to FIG. 8, this figure illustrates an automatic feedback selection tool 801 that may be employed according to various embodiments of the invention. The automatic feedback selection tool 801 includes a session time determination module 803 and an audible content selection module 805. The automatic feedback selection tool 801 cooperates with a user interface 809, a memory 811, and an audible content data storage device 813 to automatically select audible content for playback to a user by a digital music player 203 during an athletic activity session.

As discussed in detail above, various examples of the invention monitor the athletic activity of a user and generate athletic data in response. As also discussed in detail above, this athletic data may include values that describe the athletic performance of the user in units of time, such as pace or speed values. Based upon these time-dependent athletic data values, the session time determination module 803 will estimate an expected time duration of a new athletic activity session. The audible content selection module 805 will then select an amount of audible content that will match or exceed the expected time duration, and transfer the selected audible content to the digital music player 203 for playback during the athletic activity session.

Figure 9:
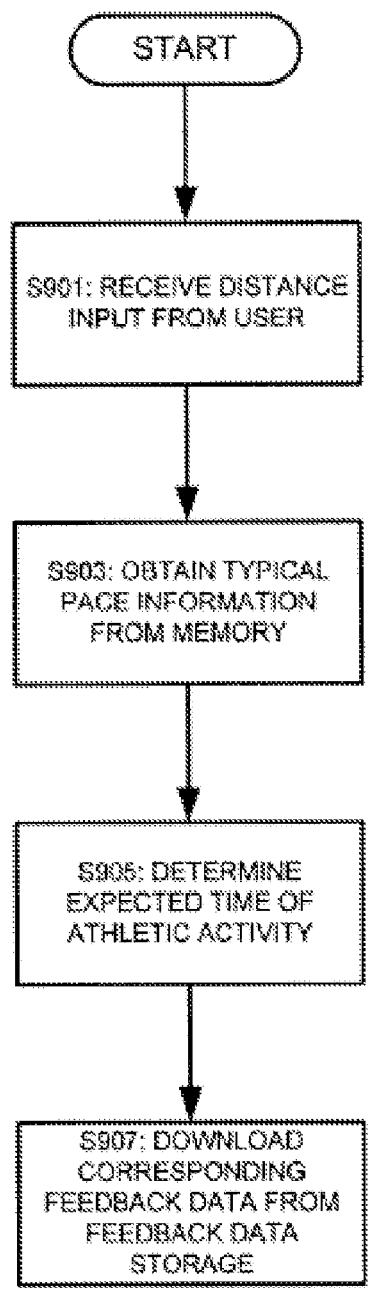
FIG. 9 illustrates a flowchart describing the operation of an automatic feedback selection tool that may be employed according to various embodiments of the invention.

The operation of the automatic feedback selection tool 801 will now be described in more detail with regard to the flowchart illustrated in FIG. 9. Initially, in step 901, the automatic feedback selection tool 801 receives athletic distance information from a user. The distance information may be provided to the session time determination module 803 through the user interface 809. The distance information may be, for example, a distance that the user intends to travel during an upcoming athletic activity session.

Next, in step 903, the session time determination module 803 obtains a time-dependent athletic data value from the memory 811. The time-dependent athletic data value may be, for example, a time-dependent athletic data value, such as a pace or speed, generated during a previous athletic activity session by the user. Alternately, the time-dependent athletic data value may be an average or other aggregation of time-dependent athletic data values from multiple previous athletic activity sessions by the user. Still further, the time-dependent athletic data value may be an arbitrary value selected by a user, such as a desired pace or speed for an upcoming athletic activity session. It should be noted that, if the time-dependent athletic data value is an arbitrary value selected by a user, then it may be input directly to the session time determination module 803 by the user through the user interface 809 rather than retrieved from the memory 811.

Next, in step 905, the session time determination module 803 uses the time-dependent athletic data value and the provided distance input to estimate a duration time of the upcoming athletic activity session. For example, if the time-dependent athletic data value is a pace of 1 mile per 12 minutes (representing, e.g., an average pace from the user's previous 25 recorded athletic activity sessions) and the user has provided a distance input of 4 miles, then the session time determination module 803 will determine the expected session duration to be 48 minutes.

In step 907, the audible content selection module 805 downloads an amount of audible content from the audible content file storage 813 that matches or exceeds the expected session duration time estimated by the session time determination module 803. Thus, with the previous example, the audible content selection module 805 will select and download at least 48 minutes or more of audible content from the audible content file storage 813 to the digital music player 203. The audible content may be selected using any desired criteria, such as a random selection, sequential selection from a playlist, or using a more sophisticated selection algorithm designed to accurately match audible content files with the expected session duration time.

It should be appreciated that, with various implementations of the invention, the session time determination module 803 and the audible content selection module 805 may implemented by, for example, software instructions executed by a computing unit 103 of a computing device 101. Also, with some examples of the invention, the session time determination module 803, the audible content selection module 805, the user interface 809 and the memory 811 may be implemented by the digital music player 203, while the audible content file storage 813 may be hosted by a separate computing device, such as a desktop or laptop personal computer. With still other examples of the invention, however, one or more of the session time determination module 803, the audible content selection module 805, the user interface 809 and the memory 811 may be implemented by the separate computing device hosting the audible content file storage 813.

Thus, various examples of the invention provide for the automatic selection of audible content for playback to a user during an athletic activity session based upon an expected time duration for that session, so that the amount of audible content available to the user is certain to match or exceed the expected time duration for the athletic activity session. It should be appreciated that, however, that while particular examples of the invention have been described with respect to audible feedback, such as music, spoken words, or other audible content, other implementations of the invention may be employed to automatically select any desired type of feedback, including visual feedback.

CONCLUSION

While the invention has been described with respect to specific examples including presently preferred modes of carrying out the invention, those skilled in the art will appreciate that there are numerous variations and permutations of the above described systems and techniques that fall within the spirit and scope of the invention.

What is claimed is:

1. A method of comparing athletic information relating to a user performing an athletic activity, the method comprising:
   receiving, by an athletic parameter measurement device, electrical signals from one or more sensors associated with the user during performance of athletic activity in a first athletic activity session;
   processing, by the athletic parameter measurement device, the electrical signals;
   transmitting, from the athletic parameter measurement device to a computing unit, the processed signals;
   generating, by the computing unit during the first athletic activity session and based on the processed signals, a first set of athletic data;
   retrieving, by the computing unit, a second set of athletic data corresponding to the first set of athletic data from baseline athletic activity data, wherein the baseline athletic activity data comprises a plurality of sets of athletic data previously generated for athletic activity performed by the user at different times during a second athletic activity session different from the first athletic activity session, and wherein the second athletic activity session is selected by the user for comparison with the first athletic activity session;

selecting, by an athletic activity feedback control unit, a time-dependent athletic data value from the second set of athletic data;

receiving, by the athletic activity feedback control unit, user input defining at least one parameter of the first athletic activity session;

determining, by the athletic activity feedback control unit, a duration of the first athletic activity session based on the at least one parameter and the time-dependent athletic data value; and selecting, by the athletic activity feedback control unit, musical content meeting the determined duration of the first athletic activity session;

comparing, by the athletic activity feedback control unit, the generated first set of athletic data with the retrieved second set of athletic data;

determining, by the athletic activity feedback control unit and based on the comparison, whether a value of at least one metric of the first set of athletic data is within a predefined proximity range relative to a corresponding value of a corresponding metric of the second set of athletic data;

selecting, by the athletic activity feedback control unit, from a spoken feedback data group including a plurality of sets of spoken feedback data, a first spoken feedback data set to audibly communicate to the user in response to determining that the value of the at least one metric of the first set of athletic data is within the predefined proximity range relative to the corresponding value of the corresponding metric of the second set of athletic data, wherein the predefined proximity range is greater than zero; and selecting, from the spoken feedback data group, a second spoken feedback data set to audibly communicate to the user in response to determining that the value of the at least one metric of the first set of athletic data is not within the predefined proximity range of the corresponding value of the corresponding metric of the second set of athletic data, the second spoken feedback data set being configured to influence the user's performance of the athletic activity relative to the first spoken feedback data set.

2. The method of claim 1, wherein the first spoken feedback data set is a default data set.

3. The method of claim 1, further including:
determining, by the athletic activity feedback control unit, a first percentage which the value of the at least one metric of the first set of athletic data deviated from the corresponding value of the corresponding metric of the second set of athletic data.

4. An apparatus for comparing athletic information relating to a user performing an athletic activity, the apparatus comprising:
at least one processor; and
memory operatively coupled to the at least one processor and storing computer readable instructions that, when executed, cause the apparatus to:
receive, by an athletic parameter measurement device, electrical signals from one or more sensors associated with the user during performance of athletic activity in a first athletic activity session;
process, by the athletic parameter measurement device, the electrical signals;
transmit, from the athletic parameter measurement device to a computing unit, the processed signals;
generate, during the first athletic activity session and by the computing unit, a first set of athletic data;
retrieve, by the computing unit, a second set of athletic data corresponding to the first set of athletic data from baseline athletic activity data, wherein the baseline athletic activity data comprises a plurality of sets of athletic data previously generated for athletic activity performed by the user at different times during a second athletic activity session different from the first athletic activity session and wherein the second athletic activity session is selected by the user for comparison with the first athletic activity session;
select, by an athletic activity feedback control unit, a time-dependent athletic data value from the second set of athletic data;
receive, by the athletic activity feedback control unit, user input defining at least one parameter of the first athletic activity session;
determine, by the athletic activity feedback control unit, a duration of the first athletic activity session based on the at least one parameter and the time-dependent athletic data value; and
select, by the athletic activity feedback control unit, musical content meeting the determined duration of the first athletic activity session;
compare, by the athletic activity feedback control unit, the generated first set of athletic data with the retrieved second set of athletic data;
determine, by the athletic activity feedback control unit and based on the comparison, whether a value of at least one metric of the first set of athletic data is within a predefined proximity range relative to a corresponding value of a corresponding metric of the second set of athletic data;
select, by the athletic activity feedback control unit, from a spoken feedback data group including a plurality of sets of spoken feedback data, a first spoken feedback data set to audibly communicate to the user in response to determining that the value of the at least one metric of the first set of athletic data is within the predefined proximity range relative to the corresponding value of the corresponding metric of the second set of athletic data, wherein the predefined proximity range is greater than zero; and
select, by the athletic activity feedback control unit, from the spoken feedback data group, a second spoken feedback data set to audibly communicate to the user in response to determining that the value of the at least one metric of the first set of athletic data is not within the predefined proximity range of the corresponding value of the corresponding metric of the second set of athletic data, the second spoken feedback data set being configured to influence the user's performance of the athletic activity relative to the first spoken feedback data set.

5. The apparatus of claim 4, wherein the first spoken feedback data set is a default data set.

6. The apparatus of claim 4, further including instructions that, when executed, cause the apparatus to:
determine, by the athletic activity feedback control unit, a first percentage which the value of the at least one metric of the first set of athletic data deviated from the corresponding value of the corresponding metric of the second set of athletic data.

\* \* \* \* \*